United States Patent
An et al.

(10) Patent No.: US 10,238,284 B2
(45) Date of Patent: Mar. 26, 2019

(54) ACQUISITION AND ANALYSIS TECHNIQUES FOR IMPROVED OUTCOMES IN OPTICAL COHERENCE TOMOGRAPHY ANGIOGRAPHY

(71) Applicant: Carl Zeiss Meditec, Inc., Dublin, CA (US)

(72) Inventors: Lin An, Walnut Creek, CA (US); Mary K. Durbin, San Francisco, CA (US); Sophie Kubach, Menlo Park, CA (US); Utkarsh Sharma, Dublin, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 15/629,502

(22) Filed: Jun. 21, 2017

(65) Prior Publication Data

US 2018/0014728 A1      Jan. 18, 2018

Related U.S. Application Data

(63) Continuation of application No. 15/015,587, filed on Feb. 4, 2016, now Pat. No. 9,700,206.
(Continued)

(51) Int. Cl.
*A61B 3/12*         (2006.01)
*A61B 3/10*         (2006.01)
(Continued)

(52) U.S. Cl.
CPC .......... *A61B 3/1233* (2013.01); *A61B 3/0025* (2013.01); *A61B 3/0041* (2013.01);
(Continued)

(58) Field of Classification Search
CPC .......... A61B 3/14; A61B 3/0025; A61B 3/12; A61B 3/102; A61B 3/0058
(Continued)

(56) References Cited

U.S. PATENT DOCUMENTS 6,549,801 B1   4/2003   Chen et al.
7,301,644 B2   11/2007  Knighton et al.
(Continued)

OTHER PUBLICATIONS

Debuc, Delia Cabrera., "A Review of Algorithms for Segmentation of Retinal Image Data Using Optical Coherence Tomography", Image Segmentation, InTech, Chapter 2, 2011, pp. 15-54.
(Continued)

*Primary Examiner* — Mohammed A Hasan
(74) *Attorney, Agent, or Firm* — Morrison & Foerster LLP

(57) ABSTRACT

Methods for improved acquisition and processing of optical coherence tomography (OCT) angiography data are presented. One embodiment involves improving the acquisition of the data by evaluating the quality of different portions of the data to identify sections having non-uniform acquisition parameters or non-uniformities due to opacities in the eye such as floaters. The identified sections can then be brought to the attention of the user or automatically reacquired. In another embodiment, segmentation of layers in the retina includes both structural and flow information derived from motion contrast processing. In a further embodiment, the health of the eye is evaluating by comparing a metric reflecting the density of vessels at a particular location in the eye determined by OCT angiography to a database of values calculated on normal eyes.

10 Claims, 6 Drawing Sheets

Related U.S. Application Data

(60) Provisional application No. 62/112,585, filed on Feb. 5, 2015.

(51) Int. Cl.
*A61B 3/00* (2006.01)
*G06T 7/00* (2017.01)

(52) U.S. Cl.
CPC ............ *A61B 3/102* (2013.01); *G06T 7/0014* (2013.01); *G06T 2207/10101* (2013.01); *G06T 2207/20044* (2013.01); *G06T 2207/30041* (2013.01)

(58) Field of Classification Search
USPC .......................................................... 351/206
See application file for complete search history.

(56) References Cited

U.S. PATENT DOCUMENTS

| | | | |
|---|---|---|---|
| 8,079,711 B2 | 12/2011 | Stetson et al. | |
| 8,857,988 B2 | 10/2014 | Sharma et al. | |
| 9,033,510 B2* | 5/2015 | Narasimha-Iyer | A61B 3/102 351/206 |
| 2005/0171438 A1 | 8/2005 | Chen et al. | |
| 2010/0027857 A1 | 2/2010 | Wang | |
| 2012/0274897 A1 | 11/2012 | Narasimha-Iyer et al. | |
| 2012/0274898 A1* | 11/2012 | Sadda | A61B 3/102 351/206 |
| 2012/0277579 A1 | 11/2012 | Sharma et al. | |
| 2012/0307014 A1 | 12/2012 | Wang | |
| 2013/0301000 A1 | 11/2013 | Sharma et al. | |
| 2013/0301008 A1 | 11/2013 | Srivastava et al. | |
| 2015/0062590 A1 | 3/2015 | Bagherinia | |
| 2016/0040977 A1 | 2/2016 | An et al. | |
| 2016/0242638 A1 | 8/2016 | Durbin et al. | |
| 2017/0035286 A1 | 2/2017 | Meyer et al. | |

OTHER PUBLICATIONS

Enfield et al., "In Vivo Imaging of the Microcirculation of the Volar Forearm Using Correlation Mapping Optical Coherence Tomography (cmOCT)", Biomedical Optics Express, vol. 2, No. 5, May 1, 2011, pp. 1184-1193.

Jia et al., "Split-Spectrum Amplitude-Decorrelation Angiography with Optical Coherence Tomography", Optics Express, vol. 20, No. 4, Feb. 13, 2012, pp. 4710-4725.

Lujan et al., "Revealing Henle's Fiber Layer Using Spectral Domain Optical Coherence Tomography", Investigative Ophthalmology & Visual Science, vol. 52, No. 3, Mar. 2011, pp. 1486-1492.

Mariampillai et al., "Speckle Variance Detection of Microvasculature using Swept-Source Optical Coherence Tomography", Optics Letters, vol. 33, No. 13, Jul. 1, 2008, pp. 1530-1532.

Nam et al., "Complex Differential Variance Algorithm for Optical Coherence Tomography Angiography", Biomedical Optics Express, vol. 5, No. 11, Nov. 1, 2014, pp. 3822-3832.

Non-Final Office Action received for U.S. Appl. No. 15/015,587, dated Nov. 10, 2016, 9 pages.

Notice of Allowance received for U.S. Appl. No. 15/015,587, dated Mar. 10, 2017, 8 pages.

Zhang et al., "Minimizing Projection Artifacts for Accurate Presentation of Choroidal Neovascularization in OCT Micro-Angiography", Biomedical Optics Express, vol. 6, No. 10, Oct. 1, 2015, pp. 4130-4143.

* cited by examiner

ACQUISITION AND ANALYSIS TECHNIQUES FOR IMPROVED OUTCOMES IN OPTICAL COHERENCE TOMOGRAPHY ANGIOGRAPHY

PRIORITY

This application is a continuation of U.S. patent application Ser. No. 15/015,587, filed Feb. 4, 2016, now U.S. Pat. No. 9,700,206 B2 which claims priority to U.S. Provisional Application Ser. No. 62/112,585 filed Feb. 5, 2015, the contents of which are hereby incorporated by reference.

TECHNICAL FIELD

The present application relates to ophthalmic imaging, and in particular to acquisition and analysis methods for vasculature image data acquired through interferometric imaging techniques such as optical coherence tomography.

BACKGROUND

Optical coherence tomography (OCT) is widely recognized as a powerful ophthalmic imaging technique. Optical coherence tomography (OCT) angiography techniques, such as optical microangiography (OMAG), speckle variance, phase variance, etc., use OCT systems to achieve the imaging of flow and motion within a tissue, including imaging of functional vascular networks within microcirculatory tissue beds in vivo, without the use of exogenous contrast agents. A majority of ocular diseases may lead to abnormality in microvasculature beds in the eye, including diabetic retinopathy (DR), age-related macular degeneration (AMD), glaucoma, retinal vein occlusion etc. OCT angiography can be a non-invasive way to be able to diagnose and monitor such vascular abnormalities. However, it is very critical to be able to obtain high quality images of vasculature and perform reliable analysis for diagnosis and monitoring of diseases.

There are several limitations in the state-of-the-art OCT angiography technology that makes it difficult to consistently acquire high quality clinical data sets. One of the major challenges of OCT angiography for larger field of view (FOV) scans is the variability of signal levels from different regions of the eye. This variability can be caused by many factors including subject motion and non-optimized refractive correction in different regions of eye. On the analysis side, there are several challenges as well, such as the capability to segment tissue layers with greater accuracy. Sometimes, spatially localized opacity, such as the one caused by a floater in the vitreous or by the opacity of the lens of the eye, may project dark pockets in the vasculature beds, thereby causing uncertainty in the diagnosis whether it is the loss of vasculature (ischemia) or shadow by a floater. In addition it will also be desirable to be able to develop analyses that could aid in detecting early vasculature based symptoms due to a disease like DR.

SUMMARY

This application describes various acquisition and analysis techniques to improve the output of OCT angiography. These are described as follows:

Increased uniformity of OCT angiography data collected over large FOV in the eye: During long acquisitions in OCT angiography over large FOVs, either in single cube or montage type acquisitions, the likelihood of non-uniform acquisition increases because of many reasons. The patients get tired and the signal may vary in different regions of the eye, due to factors including Z-motion, pupil shifts, non-optimized focus, irregular tear film due to drying during the setup and acquisition of images, shadowing etc. Methods are described to ensure increased uniformity in data quality over large FOVs. In one approach, regions of low signal data are identified after the scan is finished and the data is reacquired from the identified region.

Identify shadow artifacts for improved assessment of capillary non-perfusion in OCT angiography: One of the issues when looking into OCT angiography images to assess non-perfusion is when there is a shadowing effect from some opacity in the path of the light, such as a floater in the vitreous etc. We can identify the enface region that is impacted by the shadow artifact and let the user know that in this region, the vasculature mapping of the tissue is not reliable. Hence, false positives caused by floaters or other media opacities can be minimized.

Improved segmentation capabilities by using motion-contrast data for segmentation purposes: Typical segmentation algorithms are based on structural or intensity OCT data. However, for some anatomical layers such as choriocapillaris etc., structural OCT data may not provide sufficient information for tissue layer differentiation, or may not provide information with as good definition in the axial direction. For tissue layers that contain vasculature beds, it will be useful to analyze motion-contrast data to be able to segment those layers. Information about the segmented layers from intensity OCT data may be used as an input to further aid the segmentation based on motion-contrast data. In the preferred embodiment, RPE information from the intensity OCT data can be used to localize the region of interest for segmentation of choriocapillaris data based on motion-contrast data.

Eye Health Indication: It is possible to compare the density of the microvasculature around the fovea to a database of normal eyes to determine if there may be damage related to diabetes or other diseases. In particular, this could potentially be done without a full cube scan of the macula. A circle scan at a particular distance from the fovea may be sufficient to distinguish the status of the eye, which could be done with a slower OCT system. Because only a cluster of circle scans of a single radius is acquired, it may be possible to dispense with tracking. A slow system with no tracking could be relatively inexpensive.

DETAILED DESCRIPTION

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

The OCT system may comprise any type of OCT system. Examples of the OCT systems may include Time-domain OCT (TD-OCT) and Fourier-domain, or Frequency-domain, OCT (FD-OCT). Examples of the FD-OCT may include spectral-domain OCT (SD-OCT), swept Source OCT (SS-OCT), and optical frequency domain Imaging (OFDI). The OCT technique can involve point scanning, line scanning, partial field scanning, or full field illumination of light on a sample.

Figure 1:
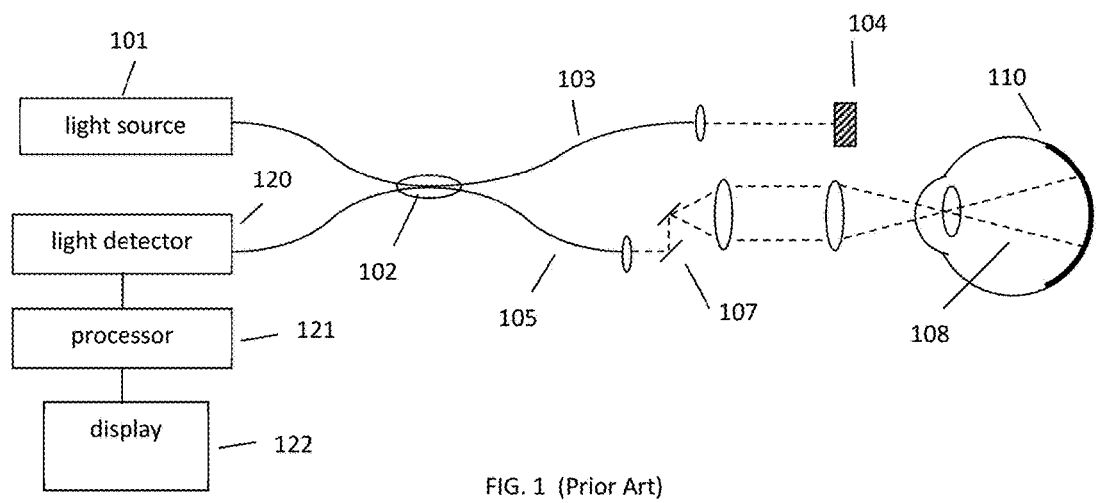
FIG. 1 illustrates a generalized OCT system that can be used to collect OCT angiography data.

A diagram of a generalized OCT system is shown in FIG. 1. Light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector is supplied to a processor 121. The results can be stored in the processor 121 or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device. The processor may contain for example a field-programmable gate array (FPGA), a digital signal processor (DSP), an application specific integrated circuit (ASIC), a graphics processing unit (GPU), a system on chip (SoC) or a combination thereof, that performs some, or the entire angiography data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of generating data for OCT angiography analysis. The techniques described herein could be applicable to any body parts, for example eye (both anterior and posterior chambers), skin, brain, muscle, cochlear, and internal organs if integrated with endoscope or catheter probe.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing motion contrast. A cluster scan can consist of multiple A-scans or B-scans collected over time at approximately the same location(s) on the sample. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

In OCT Angiography (a.k.a. Functional OCT, optical microangiography, motion contrast OCT), changes between the OCT data collected at the same location at different times (cluster scans) are used to analyze motion or flow in the sample using any one of a multitude of motion contrast algorithms (see for example US Patent Publication Nos.

2005/0171438, 2012/0307014, 2010/0027857, 2012/0277579, U.S. Pat. No. 6,549,801, Mariampillai et al., "Speckle variance detection of microvasculature using swept-source optical coherence tomography", Optics Letters 33(13), 1530-1533, 2008, Enfield et al., "In vivo imaging of the microcirculation of the volar forearm using correlation mapping optical coherence tomography" (cmOCT), Biomed. Opt. Express2(5), 1184-1193, 2011, Nam et al. "Complex differential variance algorithm for optical coherence tomography angiography" Biomedical Optics Express 5(11) 3822-3832 2014, and Jia et al. "Split-spectrum amplitude decorrelation angiography with optical coherence tomography" Optics Express 20(4) 4710-4725 (2012), the contents of which are hereby incorporated by reference). Motion contrast algorithms can be applied to the intensity information derived from the OCT image data (intensity-based algorithm), the phase information from the OCT image data (phase-based algorithm), or the complex OCT image data (complex-based algorithm).

Figure 2:
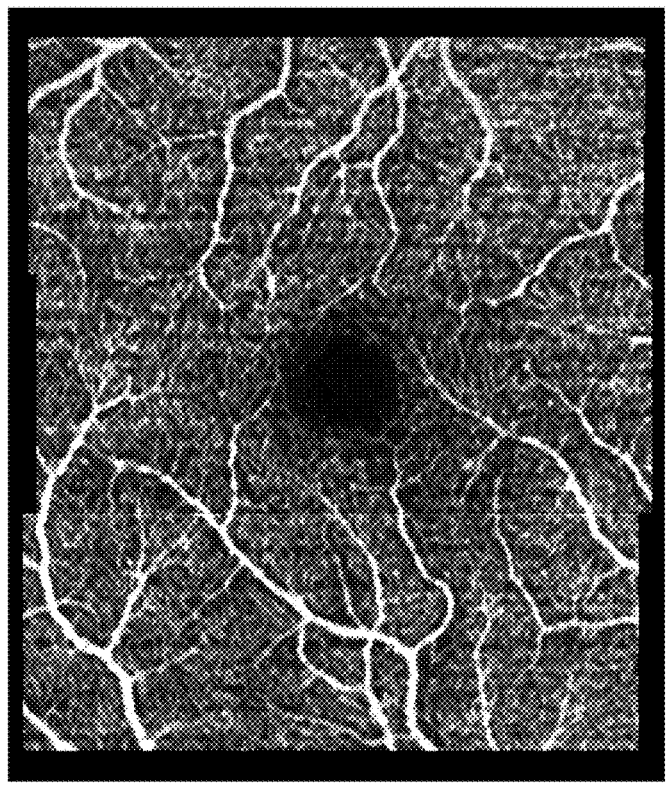
FIG. 2 shows a typical en face vasculature OCT angiography image of the retina.

An en face vasculature image is an image displaying the motion contrast signal in which the data dimension corresponding to depth is displayed as a single representative value, typically by summing or integrating an isolated portion of the data (see for example U.S. Pat. No. 7,301,644 hereby incorporated by reference). An example of an en face vasculature image is shown in FIG. 2. For this image, three volumes (cubes) of data were collected with some overlapping area in the retina. The enface images obtained from the three volumes were montaged, or combined, to create a larger field of view enface image. Each B-scan in a given data volume consists of 300 A-scans, each cluster scan consists of four B-scans, and there are a total of eighty different cluster scans. Hence, the number of A-scans in a given unit data volume are 300×80×4. After processing the data to highlight motion contrast using any one of the known motion contrast techniques, a range of 50-60 pixels corresponding to 100-120 microns of tissue depth from the surface of internal limiting membrane (ILM) in retina, are summed to generate an en face image of the vasculature. Each B-scan takes approximately 12 ms to acquire (including fly-back time) so the time between B-scans is approximately 12 ms which is on the order of interest for retinal vasculature dynamics.

There are several limitations in the state-of-the-art OCT angiography technology as well as in commercial OCT systems that makes it difficult to consistently acquire high quality clinical data sets and derive meaningful clinical analysis. This application describes various acquisition and analysis techniques to improve the results of OCT angiography imaging.

Increased uniformity of OCT angiography data collected over large FOV in the eye: During long acquisitions in OCT Angiography over a large field of view (FOV), either in single cube or montage type acquisitions, the likelihood of non-uniform acquisition conditions may increase. In U.S. Pat. No. 8,857,988, hereby incorporated by reference, we described the use of tracking to aid in the collection of OCT angiography data in both single and multiple volume acquisitions to avoid contamination from motion artifacts that become more likely the longer the scan acquisition takes. Here we propose several ideas to improve the acquisition of OCT angiography data collection over large fields of view where variations in the curvature of the eye or the focus can lead to non-uniformities in the collected data.

Figure 3:
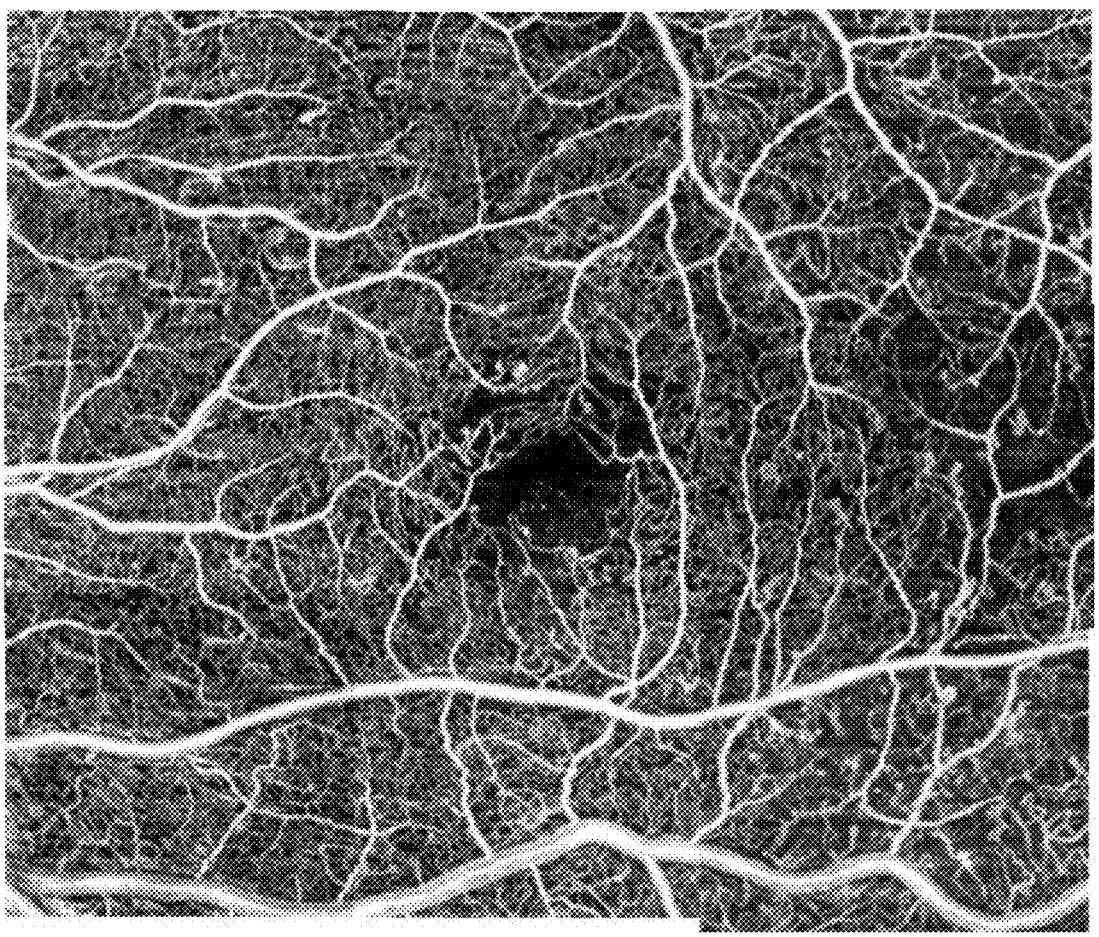
FIG. 3 shows a wide-field OCT angiography en face vasculature image of a retina having uniform imaging parameters over the entire field of view.
Figure 4:
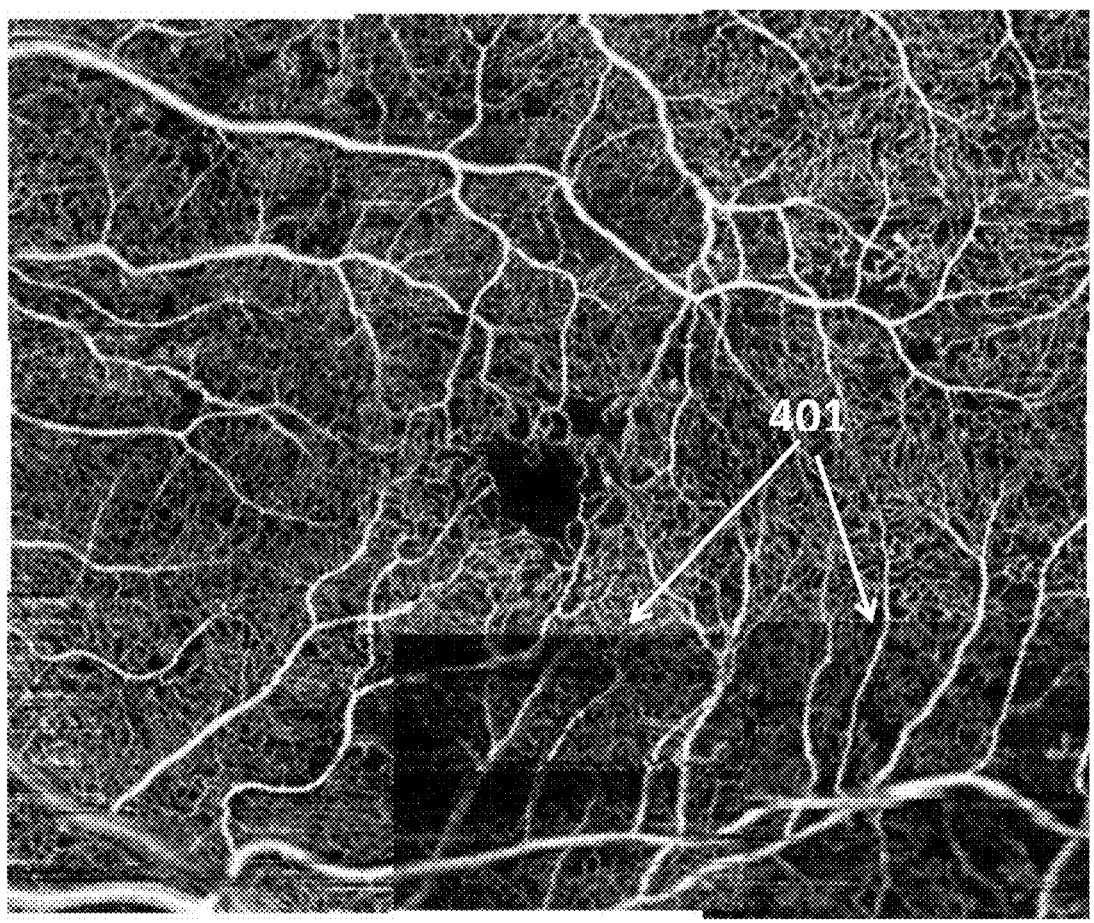
FIG. 4 shows a wide-field OCT angiography en face vasculature image of a retina where sections show non-uniform acquisition parameters relative to the rest of the data.

FIG. 3 shows a wide-field enface OCT angiography vasculature image (FOV~7 mm×6 mm) obtained by montaging of 9 data cubes in a 3×3 grid manner. It can be seen from the montage enface image that the signal characteristics are similar across the different cubes, and one could conclude that all the 9 data cubes were acquired under uniform acquisition conditions such that there were no significant Z-motion shifts, pupil shifts or non-optimized focus, etc. Hence it is possible to obtain reliable clinical information about the vasculature from this wide field image. In contrast, in the montaged image shown in FIG. 4, the middle and right cubes (401) in the bottom row had different acquisition conditions leading to significantly different data quality compared to the adjacent regions. Such an outcome will not be acceptable as it is difficult to make useful and accurate clinical diagnosis based on this image.

In one embodiment of this application, an OCT angiography data scan comprising at least one cluster scan is completed, regions of sub-optimal data (e.g. low signal data) are identified after the scan is finished, and the data is either automatically reacquired from the identified region or the operator is prompted to reacquire it, e.g. with a message displayed on the screen of the instrument. The identification of sub-optimal data can be carried out on the structural (intensity) OCT data before the motion contrast algorithm is applied to the dataset or on the processed motion contrast data. The analysis can be carried out on a single volume or cube of data or on data collected as multiple overlapping cubes. In the case of multiple overlapping cubes, the final image would result from montaging the motion contrast information resulting from processing the multiple cubes together.

To enable identification of regions of sub-optimal data regions, a quality metric can be used. In one embodiment, a quality metric is based on a comparison of the vasculature density or the signal strength at the overlap area or at the edges of two cubes. A predetermined threshold for the quality metric such as described in US Patent Publication No. 2015/0062590 hereby incorporated by reference could also be used to flag differences in acquisition parameters. Using this approach one could provide a montage 2D preview to the user after complete acquisition of the multiple image cubes, and allow or prompt the user to re-scan bad cubes. Alternatively and preferably, the system would automatically re-collect the portions of the data identified as sub-optimal, thus creating the most efficient work flow. One could also have the system automatically re-acquire only the portion of a scan that had poor signal in order to limit the total acquisition time required to collect good data.

In other approaches, one could improve uniformity of data characteristics by ensuring that the OCT beam is well-focused in different regions of the eye. In typical OCT systems, a single refractive correction is used for a given fixation. This refraction correction typically ensures that the retina near the fovea is brought into best focus for the specific optics of the eye being imaged. Because the eye is curved, when attempting to image parts of the eye away from the fovea, the distance from the pupil to the retina may change. The user will often make manual adjustments to the refractive correction of the system to obtain a better image while collecting data. The commercial OCT system Cirrus HD-OCT (ZEISS) offers an AutoFocus capability which can be applied on peripheral scans as well as fovea-centered scans, but this feature takes 1-2 seconds to use. Such optimizations may be critical to ensure uniformity in OCT angiography, especially when collecting multiple images over different parts of the eye to cover a wide-field of view. It is desirable to automate the optimizations to avoid the need for manual adjustment and to avoid taking 1-2 seconds per scan type to perform the optimization. In an OCT B-scan, the retina often appears curved. This is due to a mismatch between the arc drawn by the OCT beam and the curvature of the portion of the eye being imaged (see for example Lujan et at. "Revealing Henle's Fiber layer using spectral domain optical coherence tomography" IOVS 52(3) 1486-1492, 2011). Because the observed curvature in the scan is related to the shape of the eye, and the shape of the eye affects the refractive correction required to bring the retina into focus, it may be possible to pre-determine the amount of adjustment to the refractive error for a neighboring scan based on the curvature of the eye observed at the edge of one of the scans already acquired. This would be faster and easier than manually adjusting with each acquisition or using AutoFocus. In one embodiment, refractive corrections are individually optimized automatically for different cubes within a montage scan by acquiring at least two OCT angiography volumes over partially overlapping locations of the eye, where for each volume the system identifies the curvature of the scan at the edge to be overlapped with the subsequent scan and adjusts the refractive correction (e.g. moving the position of the ocular lens) established at the start of scanning to account for the observed curvature.

Another optimization that is frequently required when acquiring multiple images over the retina is adjustment of the position of the pupil. The position of the pupil may affect the amount of light that is able to reach the portion of the retina being scanned. When part of the beam is cut off by the patient pupil this is called vignetting. The position of the pupil also affects the apparent tilt of the retina in the OCT B-scan as described above—the OCT beam arc is scanned through a point on the pupil, and the curve drawn out will depend on the line between the pupil entry position and the back of the eye. It is difficult to maintain a steady relationship between these two over long periods of time, and in practice the instrument operator often has to adjust the pupil entry position between scans. Automatically tracking the relationship between the beam and the pupil would ensure the beam remains within the pupil, which prevents vignetting. Tracking the pupil can also be used to ensure that the retina is as perpendicular to the incident beam as can be achieved. Avoiding tilt of the retinal relative to the image should help with stitching together multiple images. To deal with these issues, in another embodiment of the present application, pupil tracking may be used to ensure uniform acquisition (see US Patent Publication No. 20120274897 hereby incorporated by reference). Pupil tracking can be used to select an optimized pupil entry location and maintain it during scanning. Pupil tracking would effectively allow the system to flatten the retina as it scans over a wide field of view. Because the optimal pupil position will vary with the patient's fixation, pupil position should be adjusted (automatically or manually) as appropriate for each fixation position.

Identify shadow artifacts for improved assessment of capillary non-perfusion in OCT angiography:

Shadowing effects from opacities in the path of light (e.g. floaters in the vitreous or cataracts), can complicate the interpretation of OCT angiography images in assessing non-perfusion. In one embodiment of improved OCT angiography data collection, the enface region(s) that is impacted by the shadow artifact is identified and the user is informed that in this region, the vasculature mapping of the tissue is not reliable. Hence, false positives caused by floaters can be minimized.

Several methods can be used to identify the shadow regions such as generating enface maps of structural data, or displaying a map of the signal strength or segmentability within the OCT data. In yet another approach, enface maps can be generated by using linear scale OCT data. It must be noted that typical enface images in OCT are generated by using log scale OCT data. Linear scale OCT data may enhance the ability to detect shadows in the structural OCT data. Shadow regions could be identified in the image or could be displayed through the use of two color channel images, one for structure and one for function. The user may be able to qualitatively examine a structural en face image in either linear or log scale, as well as structural B-scans, to identify areas affected by floaters. In one embodiment, post-processing software would evaluate the structural and angiographic en face images and highlight areas of high or low confidence. In another embodiment, the areas of low confidence would be masked. Another option would be to alert the user to the need to re-acquire data when it was impacted by a floater, or to automatically have the software re-acquire.

In addition, adjunct imaging modalities such as line scanning ophthalmoscopy or some other form of fundus imaging, taken near simultaneously with the OCT images could be used to visualize and/or localize shadows due to floaters. The information about the location of the opacities could be displayed on the motion contrast image to convey low confidence in the data in those areas.

Figure 5:
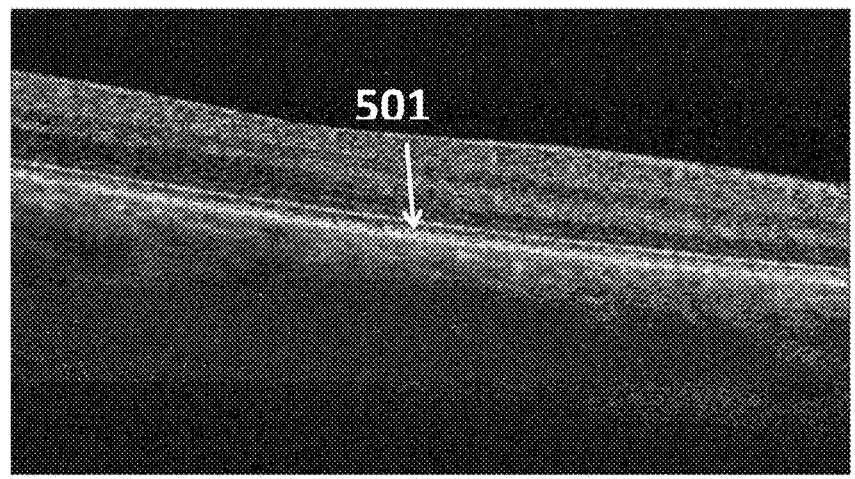
FIG. 5 shows a structural B-scan image of the retina with the retinal pigment epithelium (RPE) layer indicated.
Figure 6:
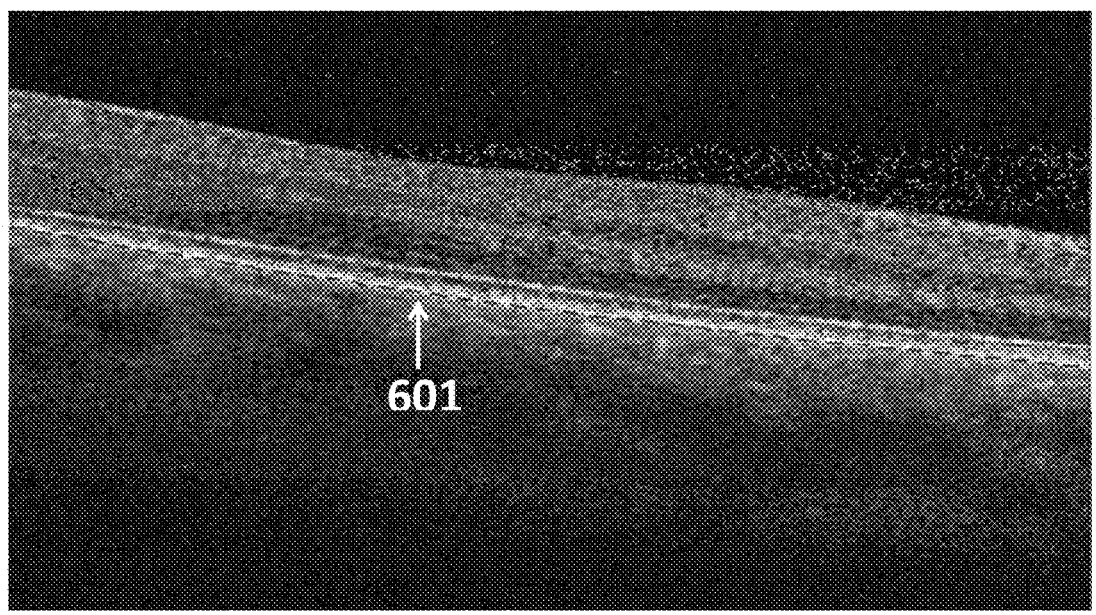
FIG. 6 shows the segmentation of the RPE on a zoomed in portion of the structural B-scan shown in FIG. 5.
Figure 7:
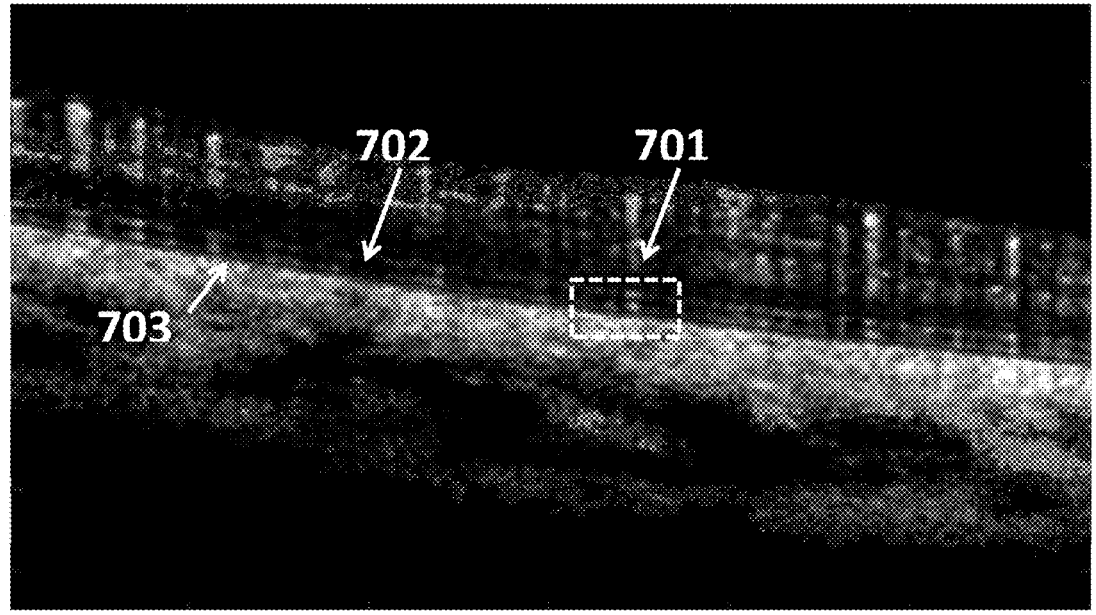
FIG. 7 shows a motion contrast B-scan of the same retina shown in FIGS. 5-6 and the segmentations from the structural and motion contrast data.

Improved segmentation capabilities by using motion-contrast data for segmentation purposes:

Segmentation algorithms are typically performed on structural or intensity OCT data (see for example 'A Review of Algorithms for Segmentation of Retinal Image Data Using Optical Coherence Tomography,' Chap. 2, in *Image Segmentation*, Ed. P.-G. Ho, Pub: InTech, 15-54 the contents of which are hereby incorporated by reference). However, for some anatomical layers such as the choriocapillaris, additional data useful to segmentation algorithms may be available in the motion contrast data. An OCT cross sectional intensity image (B-scan) is shown in FIG. 5. This image consists of 300 A-scans. Based on microstructure information of the OCT intensity image, the center of the retinal pigment epithelium (RPE) layer (501) is typically segmented as the dash line 601 shown in FIG.6. Although it looks like it accurately locates the position of RPE, it is not good enough to segment out the choriocapillaris, the layer below the RPE. It also does not define the width of the of the RPE layer. FIG. 7 is a motion contrast image generated by applying any one of a number of OCT angiography algorithms to a plurality of OCT intensity images collected over the same region as FIG. 6. The motion contrast B-scan in FIG. 7 highlights the flow in the tissue.

The outputs of OCT angiography typically include a volume of structural data that is created by averaging B-scans from common locations as well as a volume of motion contrast or flow data that is created by comparing B-scans from the same set of locations on the sample separated in time. These two volumes are inherently co-registered and contain different information about the imaged volume of tissue. One example of additional information that is available in the flow image includes the fact that the choroid has a substantially different flow signature than the retina. This can be seen in FIG. 7, which shows the retinal tissue to be dark in the flow image, while in typical structural images such as seen in FIG. 6 the retina is bright. There is an apparent sharp break in the flow image where the retina ends and the choriocapillaris begins. This dark to bright transition could be a potentially higher resolution method for isolating the lower boundary of the RPE and upper boundary of the choriocapillaris than any segmentation of the structural information from the retina. In graph-based segmentation methods, a cost function is built up based on information such as gradients and intensity values within the structural image. A cost function that includes information from both the structural image and the flow image would contain more information than the typical segmentation cost function based only on the structural image and therefore serve as an improved segmentation approach. Two other examples where information is contained in the flow image are 1) the outer retina is expected to contain no vasculature in a normal eye, and 2) the vitreous is also expected to be vessel free.

In another embodiment of the present application, information about the segmented layers from intensity OCT data may be used as an input to further aid the segmentation based on motion-contrast data or vice versa. In the preferred embodiment, RPE information from the intensity OCT data can be used to localize the region of interest for segmentation of the choriocapillaris based on motion-contrast data. Alternately, information about the location of the vascular layers from OCT motion contrast data could be used to inform segmentations of the tissue layers that are known to contain those vascular beds, including the ability to segment the outer nuclear layer from inner retinal vasculature locations and the ability to segment Bruch's membrane from the Choriocapillaris layer.

Figure 8:
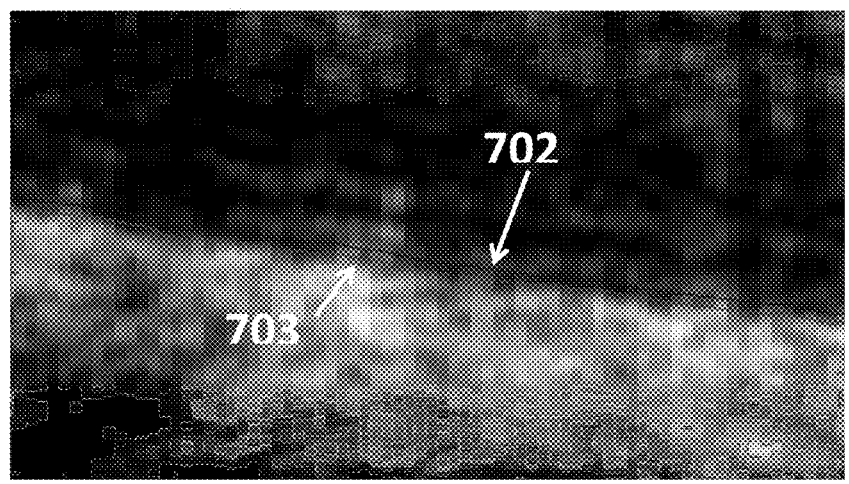
FIG. 8 is a zoomed in version of the box of data from FIG. 7.

As previously mentioned, the motion contrast B-scan in FIG. 7 highlights the flow in the tissue. Line 702 is the segmentation from FIG. 6. The sharpest edge of the motion contrast image can be identified by e.g. taking the gradient of the motion contrast image data. This line, shown as line 703 in FIG. 7, serves as a more accurate segmentation of the choriocapillaris. As can be seen in FIG. 7, the segmentation line 702 from the intensity data appears several pixels above the actual choroidcapillaris layer in the figure. FIG. 8 is a zoomed in picture of box 701 in FIG. 7 corresponding to the region enclosed by the dashed box, which further illustrates the inaccurate segmentation of choriocapillaris (703) that would be generated by directly using the RPE segmentation (702) obtained from a traditional OCT image.

A main idea of this method is to use the flow contrast image as additional information that is inherently registered to the structural image to improve identification of specific layers as well as to make it possible to identify layers and boundaries that are not well delineated in structural images. It may be necessary to correct the motion contrast image for decorrelation tails to take full advantage of this method. Such correction might involve subtracting partial en face images based on inner layers from that of outer layers that contain the decorrelation tails (see for example, Zhang, Anqi, Qinqin Zhang, and Ruikang K. Wang. "Minimizing projection artifacts for accurate presentation of choroidal neovascularization in OCT micro-angiography." *Biomedical Optics Express* 6.10 (2015): 4130-4143 hereby incorporated by reference).

Evaluating the health of an eye using vessel density:

Microvasculature in the eye is affected by diabetic retinopathy (DR). With the development of OCT angiography, the microvasculature of the eye is better visualized than in fluorescein angiography (FA), and some clinical experts have observed that the DR may be further advanced than had been appreciated in the normal clinical observations. In particular, the vessels appear less dense around the fovea for eyes with known diabetic retinopathy. Hence, a way to tell when an eye has early signs of microvascular damage is desirable. If this is possible with a regular OCT system, that is useful, but it would be even more useful if it could be done using a lower cost system.

The idea presented herein is to compare the density of the microvasculature around the fovea to a database of normal eyes to determine if there may be damage related to diabetes or other diseases. In particular, this could be done without a full cube scan of the macular region. A cluster of circle scans at a particular distance from the fovea may be sufficient to distinguish the status of the eye. This could be done with a relatively slow (<27,000 A-scans/sec) OCT system. Because only a cluster of circle scans at a single radius around the fovea is acquired, it may be possible to dispense with tracking. A slow system with no tracking could be relatively inexpensive.

In one embodiment of the present application, an OCT angiography dataset is collected, said dataset including data that surrounds the fovea of the eye. The OCT angiography dataset comprises one or more cluster scans suitable for motion contrast processing. In a preferred embodiment, the dataset comprises a cluster of circular scans centered on the fovea having a particular radius. Alternatively, the dataset could be a standard OCT data cube, comprising clusters of B-scans. The volume could be centered on the fovea, or the fovea could later be identified in the volume before processing as is well known by those skilled in the art (see for example U.S. Pat. No. 8,079,711 hereby incorporated by reference). The dataset is processed to generate vasculature information using any one of the previously described and referenced motion contrast algorithm. A metric of the density of the vasculature at one or more locations is determined. This metric is then compared to a database of density values determined from a collection of normal eyes, and the results of the comparison are stored or displayed to the user.

The density could be determined from motion contrast analysis of OCT data (See for example US Patent Publication No. 2013/0301008 the contents of which are hereby incorporated by reference). The density can be estimated by creating a skeletonized version of the vasculature image. This can be done by applying a Hessian filter or by other image processing techniques that binarize the image. The binarized image may be proportional to the size of the vessels in two dimensions, or it may allow each vessel to be only one pixel wide. This prevents saturation of the calculation based on larger vessels that are not relevant to the microvascular profile. Once the map is binarized, an elliptical calculation profile is estimated from the boundary of the foveal avascular zone, and the density is averaged around one or more ellipses at given distances from the boundary of the FAZ. The foveal avascular zone in a motion contrast image can be automatically determined (see for example US Patent Publication No. 2013/0301008 hereby incorporated by reference).

Figure 9A:
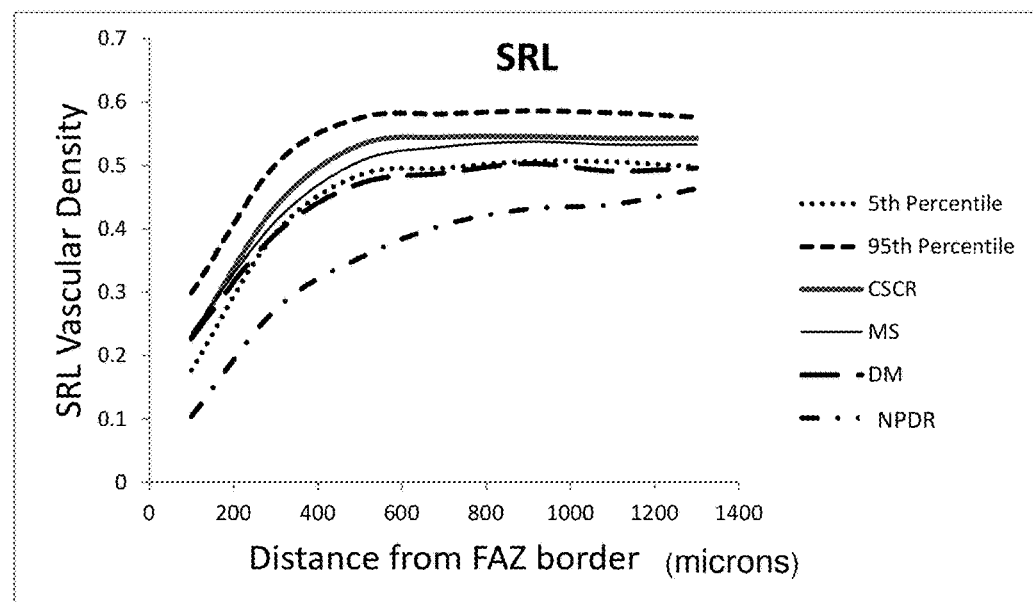
FIG. 9a illustrates the vasculature density of the superficial retinal layer (SRL) as a function of distance from the boundary of the foveal avascular zone for a plurality of eyes and two normative limits.
Figure 9B:
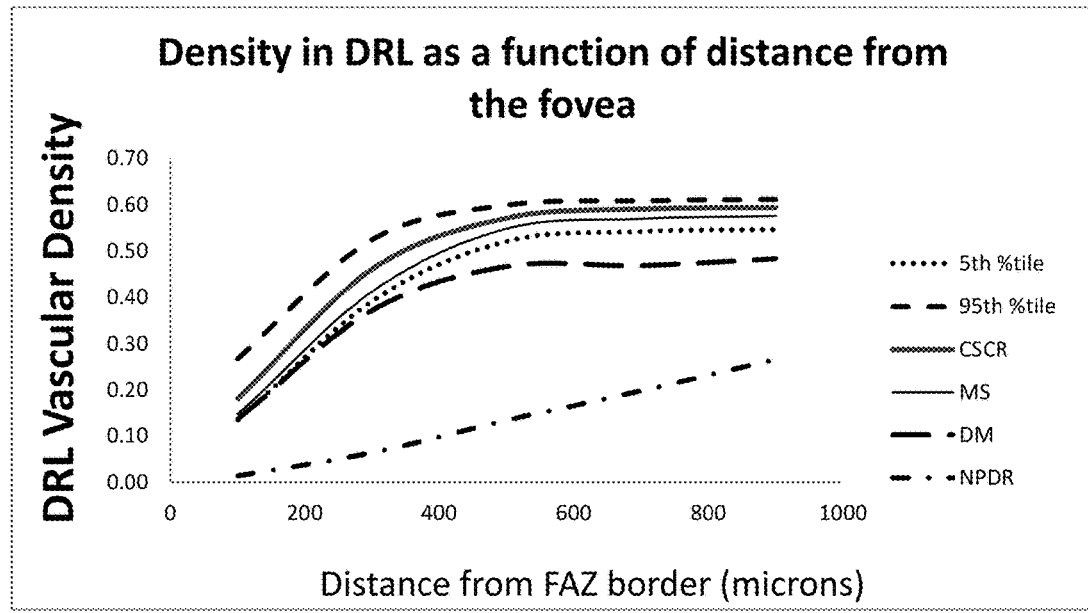
FIG. 9b illustrates the vasculature density of the deeper retinal layer (DRL) as a function of distance from the boundary of the foveal avascular zone for a plurality of eyes and two normative limits.

FIGS. 9a and 9b show the microvascular density of the macula as a function of distance from the boundary of the foveal avascular zone for a few different cases. FIG. 9a shows the data for the superficial retinal layer (SRL) and FIG. 9b shows the data for the deeper retinal layer (DRL). In general, the density starts low and increases away from the fovea. The upper and lower 5% limits of the density for a small population of normal eyes is shown (dotted for $5^{th}$ percentile and dashed for $95^{th}$ percentile). Overlaid on this normative data are the same plots for an eye with non-proliferative diabetic retinopathy (NPDR, dotted dashed), and an eye with early diabetes, but no signs of retinopathy (DM, long dashed), as well as an eye with a history of central serous retinopathy (CSCR, solid bold) and one from a subject with multiple sclerosis (MS, solid unbold). The fact that the eye from a subject with a history of very early diabetes and no retinopathy (DM case) is below normal for SRL and well below normal for DRL away from the fovea supports that a metric based on this information might be useful for evaluating the health of the eye, such as screening for pathologies or wellness monitoring. Examining these plots, it is clear that a cluster of circle scans that could identify and quantify the density of vasculature at ~600 um from the foveal avascular zone could be a rapid way to measure the health of the eye, at least as it may be affected by diabetes. Additional information may be gleaned by reviewing the entire profile, or a map of the density, in both cases benefiting from a comparison to reference databases.

Although various applications and embodiments that incorporate the teachings of the present invention have been shown and described in detail herein, those skilled in the art can readily devise other varied embodiments that still incorporate these teachings.

What is claimed is:

1. A method for acquiring wide-field optical coherence tomography (OCT) angiography image data of an eye using an OCT system having an adjustable refractive correction, comprising:

acquiring a first OCT angiography volume dataset with the OCT system at a first refractive correction over a first region of the eye, said OCT system including a light source generating a light beam that is divided into sample and reference paths, said OCT system including a detector for monitoring light received from the sample and reference paths, said detector generating output signals in response to the monitored light, said OCT system further including a processor for analyzing the output signals;

in said processor, determining a curvature of the eye from the first volume dataset near an edge of the first region;

in said processor, determining a second refractive correction based on the determined curvature;

acquiring a second OCT angiographic volume dataset with the OCT system at the second refractive correction over a second region of the eye different from the first region, said second region at least partially overlapping the edge of the first region;

generating a single image of the eye from the first and second datasets; and storing in the processor the generated image or a further analysis thereof or displaying on a display the generated image or a further analysis thereof.

2. The method as recited in claim 1, further comprising repeating the acquiring and curvature determining steps for a plurality of partially overlapping regions wherein the determined curvature near an edge of the most recently acquired OCT angiographic volume data set is used to determine a refractive correction value to be used with the subsequently acquired OCT angiographic volume data set and wherein the OCT angiographic volume data sets are combined to generate a single image of the eye.

3. A method for displaying optical coherence tomography (OCT) angiography image data to a user comprising:

acquiring an OCT angiography data set of a region of an eye using an OCT system, said OCT system including a light source generating a light beam that is divided into sample and reference paths, said OCT system including a detector for monitoring light received from the sample and reference paths, said detector generating output signals in response to the monitored light, said OCT system further including a processor for analyzing the output signals;

generating an en face image from the OCT angiography data set;

identifying regions in the image having shadow artifacts; and displaying on a display the en face image wherein the regions on the en face image identified to have shadow artifacts are identified to the user in the displayed en face image.

4. The method as recited in claim 3, further comprising generating an en face image of structural data from the OCT angiography dataset and wherein the identifying step involves using the en face structural data.

5. The method as recited in claim 4, wherein the en face image of structural data is generated using linear scale OCT data.

6. The method as recited in claim 3, further comprising acquiring an image of the same region of an eye using an adjunct imaging modality and wherein the identifying step includes using the image from the adjunct imaging modality.

7. The method as recited in claim 6, wherein the adjunct imaging modality is line scanning ophthalmoscopy.

8. The method as recited in claim 3, wherein the displaying step involves displaying two color channel images, one for structure and one for function.

9. The method as recited in claim 3, further comprising reacquiring the OCT angiography dataset or a portion thereof based upon the identification of shadow artifacts.

10. The method as in 3, further comprising generating a mask of regions affected by shadow artifacts and excluding them from any further quantitative analysis or display.

* * * * *

UNITED STATES PATENT AND TRADEMARK OFFICE
CERTIFICATE OF CORRECTION

PATENT NO. : 10,238,284 B2
APPLICATION NO. : 15/629502
DATED : March 26, 2019
INVENTOR(S) : Lin An et al.

It is certified that error appears in the above-identified patent and that said Letters Patent is hereby corrected as shown below:

In the Specification

In Column 8, Line 45, delete "of the of the" and insert -- of the --, therefor.

In Column 9, Line 37, delete "choroidcapillaris" and insert -- choriocapillaris --, therefor.

In the Claims

In Column 12, Line 47, in Claim 10, delete "in 3" and insert -- in claim 3 --, therefor.

Signed and Sealed this
First Day of September, 2020

Andrei Iancu
*Director of the United States Patent and Trademark Office*